(12) United States Patent
Palmatier et al.

(10) Patent No.: US 10,322,012 B2
(45) Date of Patent: Jun. 18, 2019

(54) SURGICAL INSTRUMENT AND METHOD

(71) Applicant: WARSAW ORTHOPEDIC, INC., Warsaw, IN (US)

(72) Inventors: Stanley T. Palmatier, Olive Branch, MS (US); William D. Armstrong, Memphis, TN (US); Anthony J. Melkent, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/705,634

(22) Filed: Sep. 15, 2017

(65) Prior Publication Data

US 2018/0085233 A1 Mar. 29, 2018

Related U.S. Application Data

(63) Continuation of application No. 15/274,672, filed on Sep. 23, 2016, now Pat. No. 10,004,609.

(51) Int. Cl.
*A61F 2/46* (2006.01)
*A61F 2/30* (2006.01)

(52) U.S. Cl.
CPC ... *A61F 2/4611* (2013.01); *A61F 2002/30471* (2013.01); *A61F 2002/30565* (2013.01); *A61F 2002/4615* (2013.01); *A61F 2002/4623* (2013.01); *A61F 2002/4627* (2013.01); *A61F 2002/4632* (2013.01); *A61F 2002/4635* (2013.01); *A61F 2002/4668* (2013.01); *A61F 2002/4687* (2013.01); *A61F 2250/0006* (2013.01)

(58) Field of Classification Search
CPC ........ A61F 2/4611; A61F 2/442; A61F 2/447; A61F 2002/4615; A61F 2002/4623; A61F 2002/4632; A61F 2002/4635; A61F 2002/4687; A61F 2250/0006
USPC ..... 606/180, 249, 247, 279, 86 A, 907, 909, 606/912, 914, 96, 99, 100, 102, 10, 4, 606/105, 104; 600/429, 427, 426, 423, 600/414, 421; 408/147, 158
See application file for complete search history.

(56) References Cited

U.S. PATENT DOCUMENTS

| 6,042,582 | A  | 3/2000 | Ray |
| 6,428,544 | B1 | 8/2002 | Ralph et al. |
| 7,235,082 | B2 | 6/2007 | Bartish et al. |
| 7,481,824 | B2 | 1/2009 | Gillum et al. |
| 7,549,998 | B2 | 6/2009 | Braun |
| 7,695,478 | B2 | 4/2010 | Ralph et al. |

(Continued)

OTHER PUBLICATIONS

International Search Report for International Application No. PCT/US2017/013849 prepared Jun. 22, 2017 by ISA Korean intellectual Property Office, 189 Cheongsa-ro, Seo-gu, Daejeon, 35208, Republic of Korea.

(Continued)

*Primary Examiner* — Pedro Philogene

(57) ABSTRACT

A surgical instrument comprises a member connected with a spinal implant defining an axis. A first image guide is connected with the member and oriented relative to a sensor to communicate a signal representative of a position of the member. A second image guide is connected with the member and oriented to represent an angle measuring a second orientation of the axis relative to a first orientation. Systems, implants and methods are disclosed.

20 Claims, 12 Drawing Sheets

(56) References Cited

U.S. PATENT DOCUMENTS

| | | |
|---|---|---|
| 7,803,162 B2 | 9/2010 | Marnay et al. |
| 7,806,932 B2 | 10/2010 | Webb et al. |
| 7,892,239 B2 | 2/2011 | Warnick et al. |
| 7,959,675 B2 | 6/2011 | Gately et al. |
| 7,988,695 B2 | 6/2011 | Dye |
| 7,976,549 B2 | 7/2011 | Dye et al. |
| 8,048,084 B2 | 11/2011 | Schneid |
| 8,062,303 B2 | 11/2011 | Berry et al. |
| 8,118,872 B2 | 2/2012 | Trudeau et al. |
| 8,142,435 B2 | 3/2012 | Refai et al. |
| 8,147,554 B2 | 4/2012 | Hansell et al. |
| 8,157,845 B2 | 4/2012 | Warnick et al. |
| 8,241,364 B2 | 8/2012 | Hansell et al. |
| 8,252,060 B2 | 8/2012 | Hansell et al. |
| 8,292,959 B2 | 10/2012 | Webb et al. |
| 8,372,084 B2 | 2/2013 | Pernsteiner et al. |
| 8,382,767 B2 | 2/2013 | Wassinger et al. |
| 8,409,290 B2 | 4/2013 | Zamani et al. |
| 8,425,529 B2 | 4/2013 | Milz et al. |
| 8,444,650 B2 | 5/2013 | Warnick et al. |
| 8,506,629 B2 | 8/2013 | Weiland |
| 8,545,566 B2 | 10/2013 | Niemiec et al. |
| 8,603,175 B2 | 12/2013 | Thibodeau |
| 8,673,012 B2 | 3/2014 | Smith et al. |
| 8,771,282 B2 | 7/2014 | Blain et al. |
| 8,864,829 B1 | 10/2014 | Bruffey et al. |
| 8,956,414 B2 | 2/2015 | Asaad |
| 8,998,924 B2 | 4/2015 | Simpson et al. |
| 9,028,553 B2 | 5/2015 | Lindenmann et al. |
| 9,095,385 B2 | 8/2015 | Wallenstein et al. |
| 9,119,729 B2 | 9/2015 | Falahee |
| 9,345,587 B2 | 5/2016 | Mitchell |
| 10,004,609 B2* | 6/2018 | Palmatier ............... A61F 2/4611 |
| 2006/0235426 A1* | 10/2006 | Lim ..................... A61F 2/4465 |
| | | 606/99 |
| 2010/0285713 A1* | 11/2010 | Somerville Roberts ..................... |
| | | C11D 3/0015 |
| | | 442/96 |
| 2010/0286713 A1 | 11/2010 | Melkent et al. |
| 2012/0185045 A1* | 7/2012 | Morris .................... A61F 2/442 |
| | | 623/17.11 |
| 2012/0185046 A1 | 7/2012 | McKay |
| 2014/0172105 A1* | 6/2014 | Frasier .................. A61F 2/4611 |
| | | 623/17.16 |
| 2014/0172106 A1 | 6/2014 | To et al. |
| 2015/0100129 A1* | 4/2015 | Waugh .................. A61F 2/4455 |
| | | 623/17.16 |
| 2016/0081812 A1 | 3/2016 | Waugh et al. |
| 2016/0220389 A1 | 6/2016 | Dinville |

OTHER PUBLICATIONS

Written Opinion of the International Searching Authority for International Application No. PCT/US2017/013849 prepared Jun. 22, 2017 by ISA Korean Intellectual Property Office, 189 Cheongsa-ro, Seo-gu, Daejeon, 35208, Republic of Korea.

* cited by examiner

SURGICAL INSTRUMENT AND METHOD

CROSS-REFERENCE TO RELATED APPLICATIONS

This application is a continuation of application U.S. patent application Ser. No. 15/274,672, filed on Sep. 23, 2016, which is hereby incorporated by reference herein, in its entirety.

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument comprises a member connected with a spinal implant defining an axis. A first image guide is connected with the member and oriented relative to a sensor to communicate a signal representative of a position of the member. A second image guide is connected with the member and oriented to represent an angle measuring a second orientation of the axis relative to a first orientation. In some embodiments, surgical systems, implants and methods are provided.

BRIEF DESCRIPTION OF THE DRAWINGS

The present disclosure will become more readily apparent from the specific description accompanied by the following drawings, in which.

DETAILED DESCRIPTION

Figure 1:
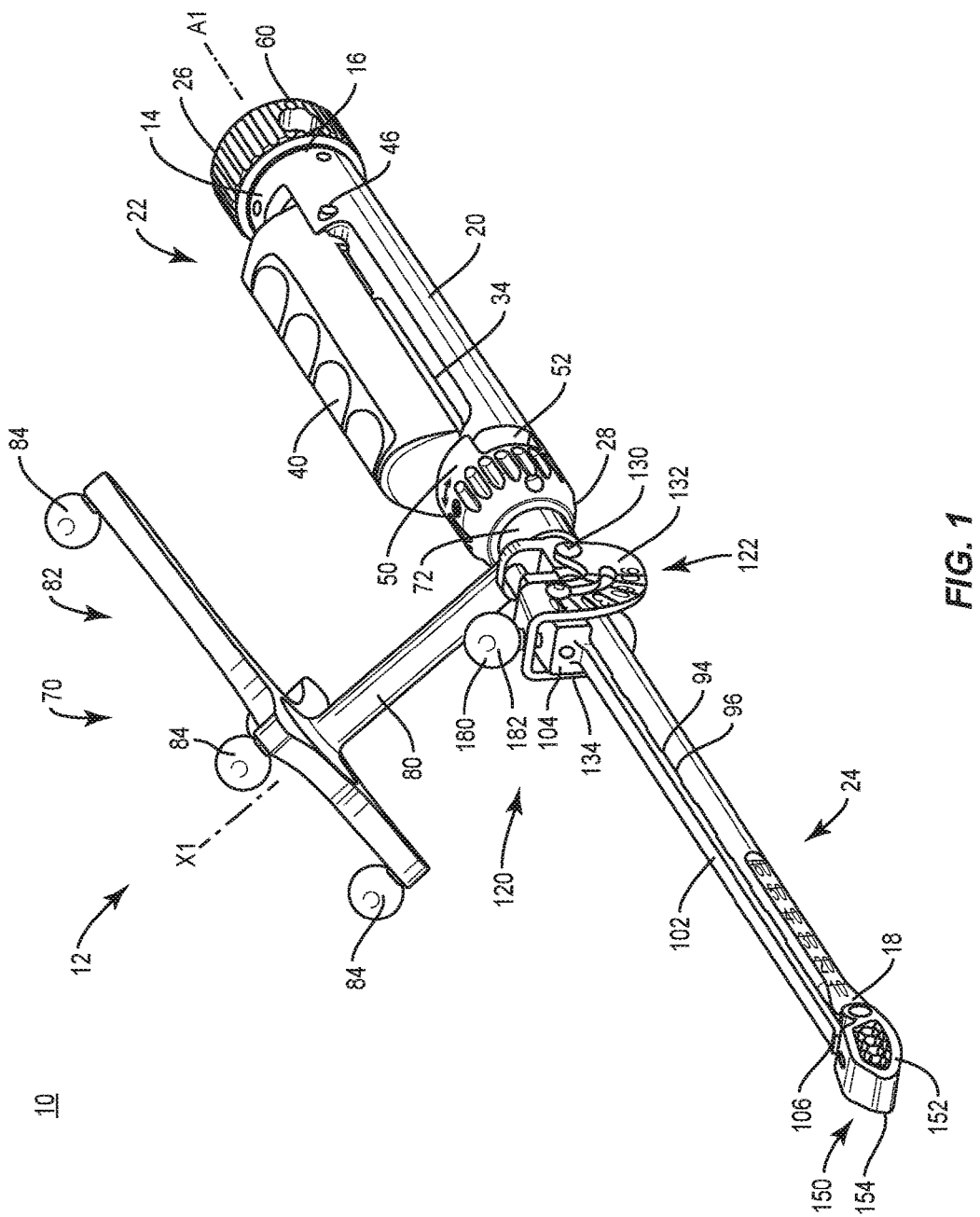
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system for preparing a surgical site, and a method for treating a spine. In some embodiments, the surgical system includes a surgical instrument having an image guide, such as, for example, a surgical navigation tracker.

In some embodiments, the surgical system includes a surgical instrument, such as, for example, an inserter employed with a selected spinal implant, such as, for example, an interbody implant, which is connected to the surgical instrument. In some embodiments, the surgical instrument includes an image guide, such as, for example, a rotational gauge. In some embodiments, the surgical instrument includes a clutch inserter with a rotational gauge.

In some embodiments, the spinal implant includes an intervertebral spacer. In some embodiments, the surgical system is employed with a method that includes manipulation, movement, translation and/or rotation of the implant with an intervertebral disc space. In some embodiments, the spinal implant includes markers for positioning and rotation. In some embodiments, the spinal implant includes a loop implant.

In some embodiments, the surgical instrument has an instrument tracker and a distal/working end. In some embodiments, the surgical tracker provides indicia and/or display of a location of the surgical instrument and its distal/working end. In some embodiments, the surgical system includes a surgical instrument having one or more image guides, which include one or more fiducial markers. In some embodiments, the fiducial marker includes a single ball-shaped marker. In some embodiments, the image guide is disposed adjacent a proximal end of the surgical instrument. In some embodiments, the image guide is attached to a longitudinal element of the surgical instrument that moves distally in a linear fashion relative to the surgical instrument and rotates the implant in the disc space. In some embodiments, the image guide provides indicia and/or display of a precise linear position of the image guide on the surgical instrument. In some embodiments, this configuration provides indicia and/or display of an amount of manipulation, movement, translation and/or rotation of the implant with tissue, such as, for example, an intervertebral space.

In some embodiments, the surgical system includes a surgical instrument having one or more image guides, which include a tracker that provides location of a surgical instrument in three dimensions, and a tracker that provides location of the surgical instrument and/or a spinal implant in two dimensions, such as, for example, a selected plane. In some embodiments, this configuration provides indicia and/or display of implant position corresponding to an amount of manipulation, movement, translation and/or rotation of the implant with tissue, such as, for example, an intervertebral space. In some embodiments, the surgical system includes a surgical instrument that comprises an inserter employed with a method for delivering an interbody spacer into an intervertebral disc space. In some embodiments, the method includes the step of manipulating, moving, translating and/or rotating the interbody spacer in a precise amount upon selected disposal of the interbody spacer in the intervertebral disc space.

In some embodiments, the surgical system includes a surgical instrument comprising a navigation compatible implant inserter. In some embodiments, the surgical system includes a surgical instrument having one or more image guides, which provide position and rotation indicia and/or display of an interbody implant via a camera sensor and a computer display screen. In some embodiments, the surgical system includes a surgical inserter that has two image guide arrays. In some embodiments, the image guide arrays interact with a navigation enabled camera sensor to provide imaging during insertion and rotation of an interbody implant. In some embodiments, the image guide arrays include a large top array used for insertion tracking of the surgical instrument, and may be used on either side of a patient. In some embodiments, the large top array is indexable for use on either side of the patient.

In some embodiments, the image guide arrays include a lower array, which provides location of the surgical instrument and/or a spinal implant. In some embodiments, the lower array includes a lower gauge shaft that translates in a linear fashion in direct contact with the implant and directly rotates a graduated gauge to provide rotational position of the implant. In some embodiments, the image guide arrays include the large top array and/or the lower array to increase the accuracy of implant placement.

In some embodiments, the surgical instrument includes a surgically navigated instrument, such as, for example, drills, drivers, and taps, which freely rotate about a centerline axis. In some embodiments, the surgical instrument includes a navigation tracker that is optically tracked and requires a line-of-sight view to a sensor, such as, for example, a camera. In some embodiments, the surgical system includes a navigation tracker attached to a surgical instrument and is disposed in a direct line of sight of a sensor, which includes one or more cameras. In some embodiments, the surgical system includes an O-arm medical imaging device that digitally captures images of an anatomy. In some embodiments, the tracker communicates with a surgical navigation system to determine and/or display surgical instrument positioning relative to the anatomy.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-7, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Figure 8:
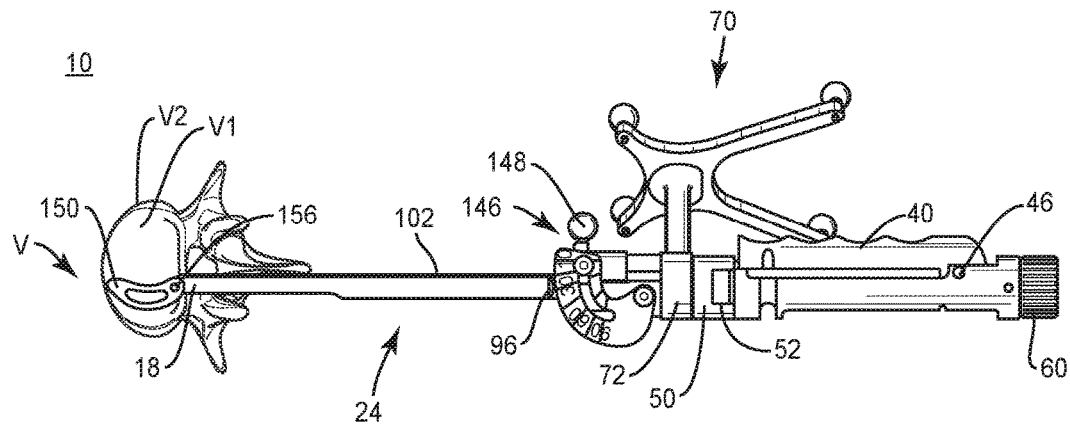
FIG. 8 is a plan view of components of one embodiment of a surgical system in accordance with the principles of the present disclosure disposed with vertebrae.
Figure 9:
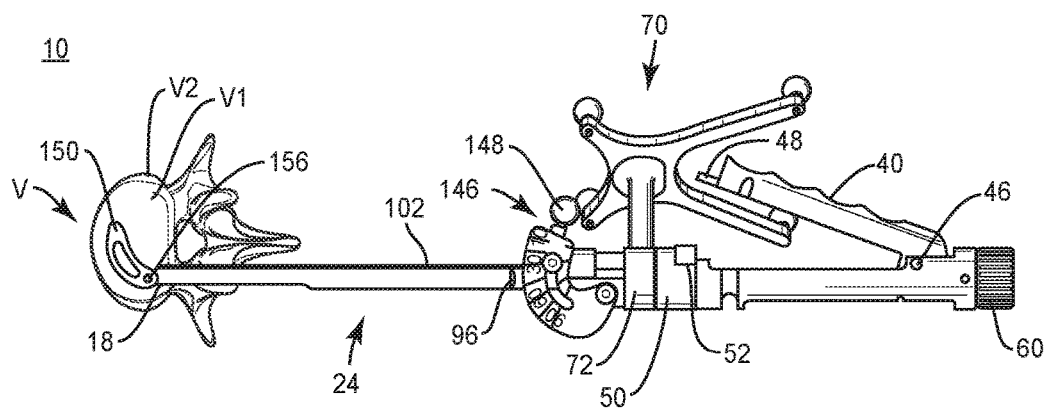
FIG. 9 is a plan view of components of one embodiment of a surgical system in accordance with the principles of the present disclosure disposed with vertebrae.
Figure 10:
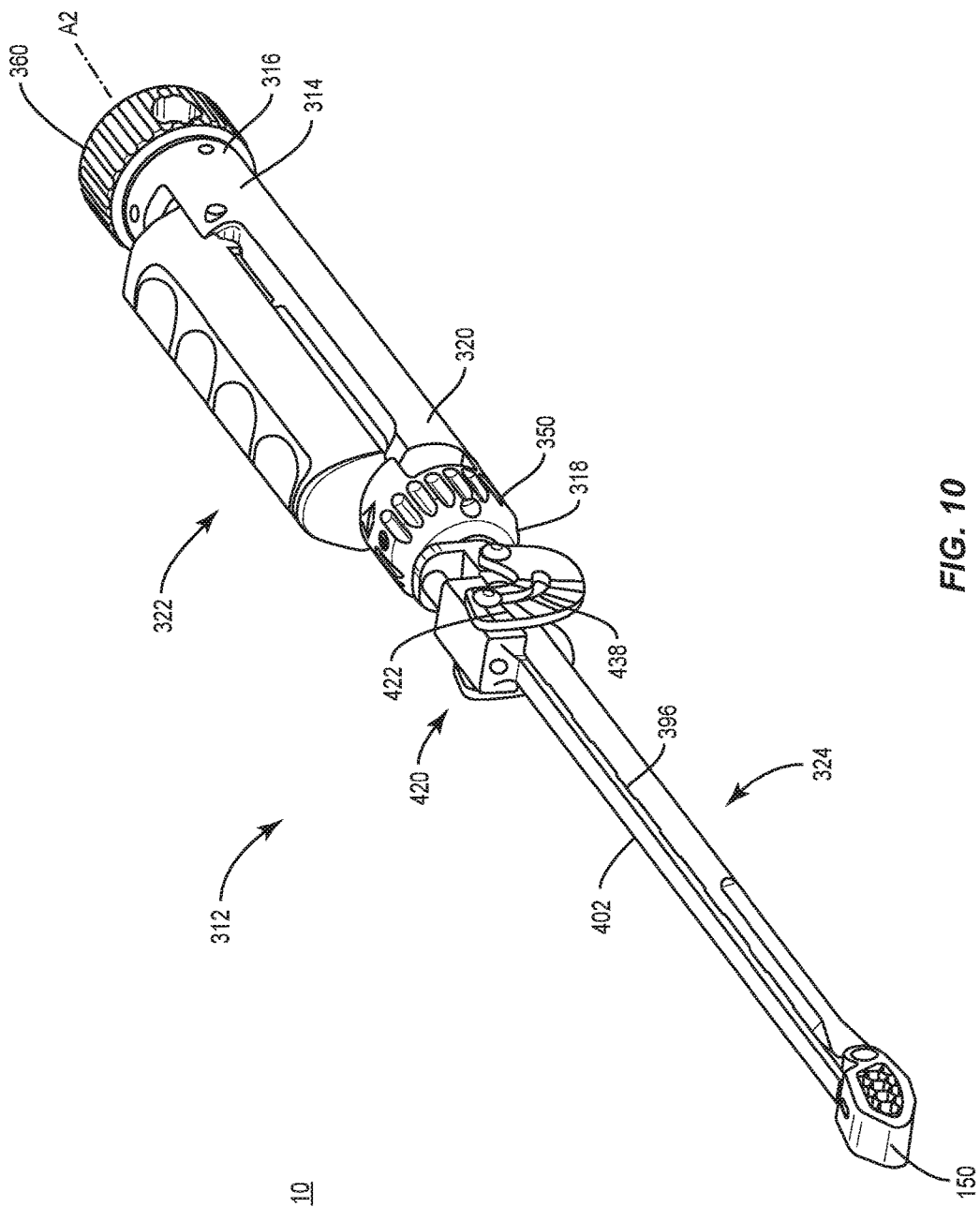
FIG. 10 is a perspective view of components of one embodiment of a surgical system in accordance with the principles of the present disclosure.

Surgical system 10 is employed, for example, with a fully open surgical procedure, a minimally invasive procedure including percutaneous techniques, and mini-open surgical techniques to deliver and introduce instrumentation and/or a spinal implant, such as, for example, an interbody implant, at a surgical site of a patient, which includes, for example, a spine having vertebrae V, as shown in FIGS. 8 and 9. In some embodiments, the spinal implant can include one or more components of one or more spinal constructs, such as, for example, cages, spacers, vertebral devices, bone fasteners, spinal rods, connectors and/or plates.

Surgical system 10 comprises a surgical instrument, such as, for example, an inserter 12. Inserter 12 includes a member, such as, for example, a body 14 that defines a longitudinal axis A1. Body 14 extends between an end 16 and an end 18. Body 14 includes an outer sleeve 20. In some embodiments, one or more portions of outer sleeve 20 may be tubular, solid and/or define cavities for disposal of components of inserter 12.

Outer sleeve 20 includes a handle 22 and a shaft 24. Handle 22 extends between an end 26 and an end 28. In some embodiments, handle 22 may have alternate cross section configurations, such as, for example, oval, oblong, triangular, square, hexagonal, polygonal, irregular, uniform, non-uniform and/or tapered. In some embodiments, handle 22 may be assembled with shaft 24, as described herein. In some embodiments, handle 22 may be monolithically formed with shaft 24. In some embodiments, handle 22 may be disposed at alternate orientations relative to shaft 24, such as, for example, transverse, parallel, perpendicular and/or other angular orientations such as acute or obtuse, co-axial, offset, and/or staggered.

Handle 22 includes a surface 30 that defines a cavity 32. Cavity 32 is configured for disposal of a longitudinal member, such as, for example, a shaft 34. Shaft 34 is configured to connect a spinal implant 150 with inserter 12, as described herein. Handle 22 is configured to facilitate manipulating, moving, translating and/or rotating spinal implant 150, as described herein. Handle 22 includes an actuator that includes a pivoting grip 40 and a knob 60, as described herein.

Grip 40 extends between an end 42 and an end 44. In some embodiments, grip 40 is ergonomically designed to be held in a plurality of orientations. In some embodiments, grip 40 includes indents configured to facilitate manipulation of grip 40. Grip 40 is connected with handle 22 at end 42 by a pin 46. End 44 includes a flange 48 configured to facilitate locking and unlocking of grip 40 relative to handle 22, as described herein.

Figure 2:
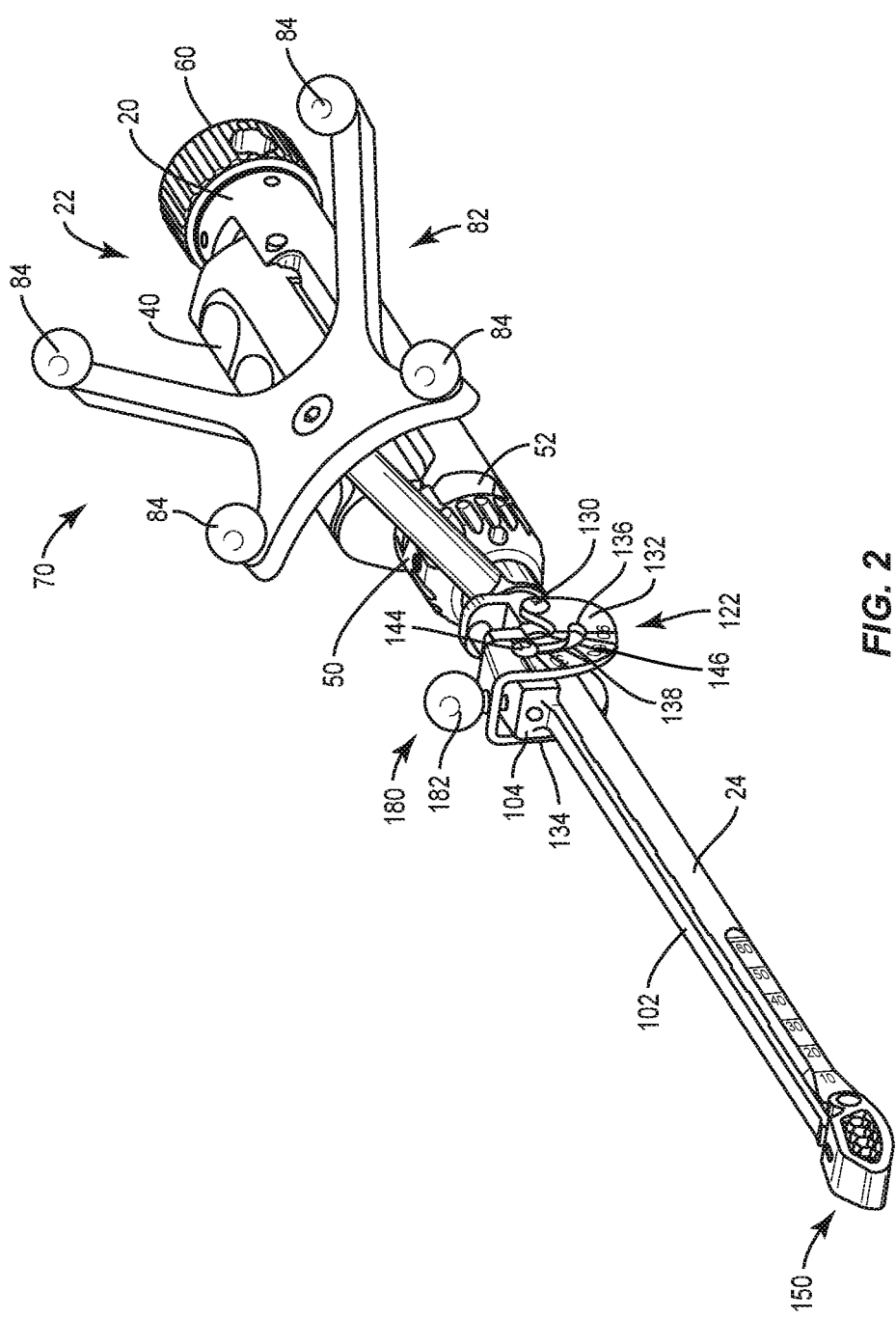
FIG. 2 is a perspective view of the components shown in FIG. 1.
Figure 3:
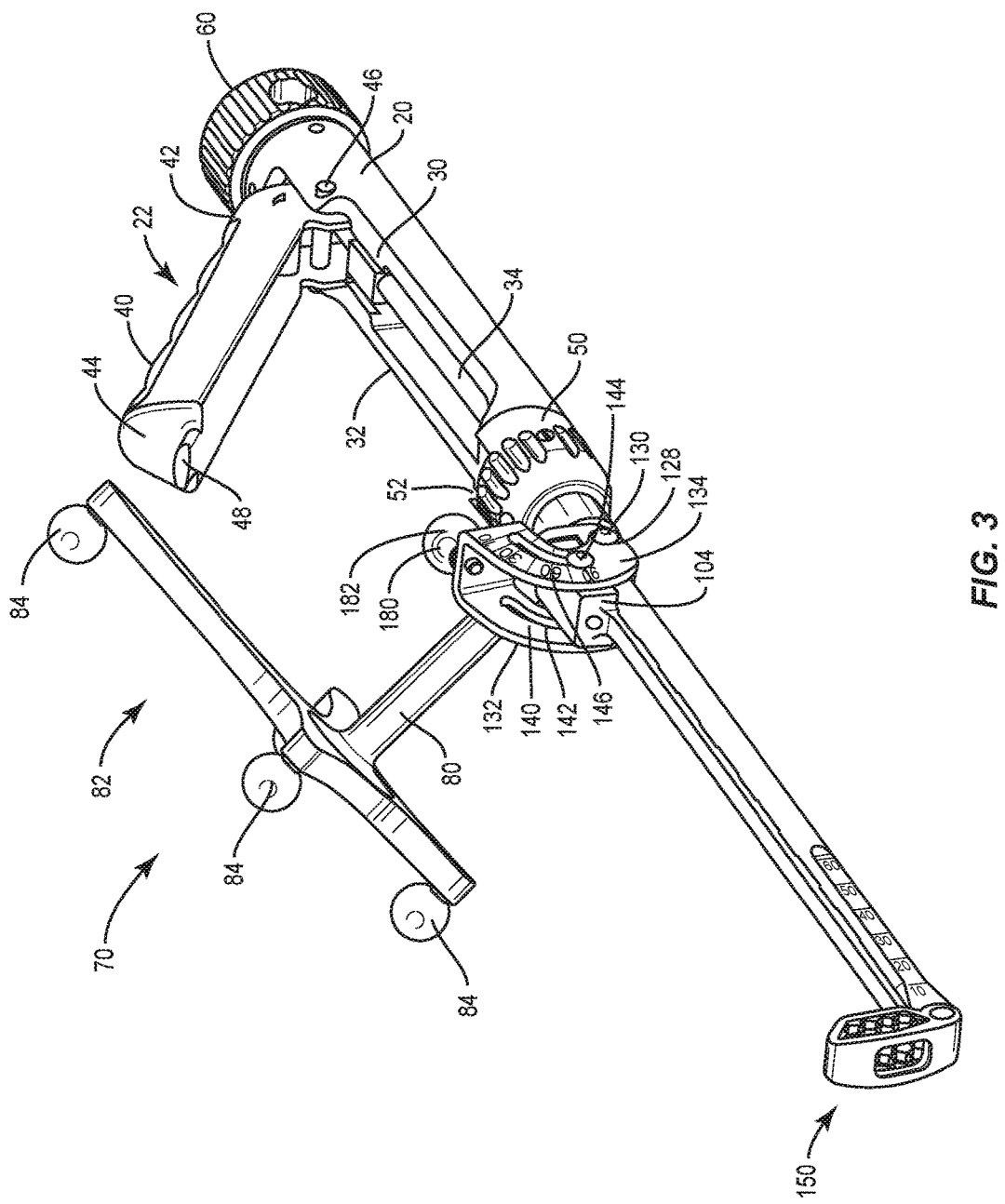
FIG. 3 is a perspective view of the components shown in FIG. 1.

Grip 40 is configured to rotate and/or pivot about pin 46 relative to axis A1. Grip 40 rotates about pin 46 between a locking orientation, as shown in FIG. 2, and a non-locking orientation, as shown in FIG. 3, of grip 40 with shaft 34. Locking of grip 40 resists and/or prevents translation of shaft 34, for example, such that spinal implant 150 is disposed in a selected and fixed position relative to end 18, as described herein. Rotating grip 40 into a non-locking orientation allows for movement and/or translation of shaft 34 relative to body 14 to facilitate movement and/or rotation of spinal implant 150 relative to end 18, as described herein. In some embodiments, grip 40 may be rotated through an angular range of 0-90 degrees relative to axis A1. In some embodiments, grip 40 may have various configurations, such as, for example, solid, tubular, arcuate, offset, staggered, uniform and non-uniform.

Figure 4:
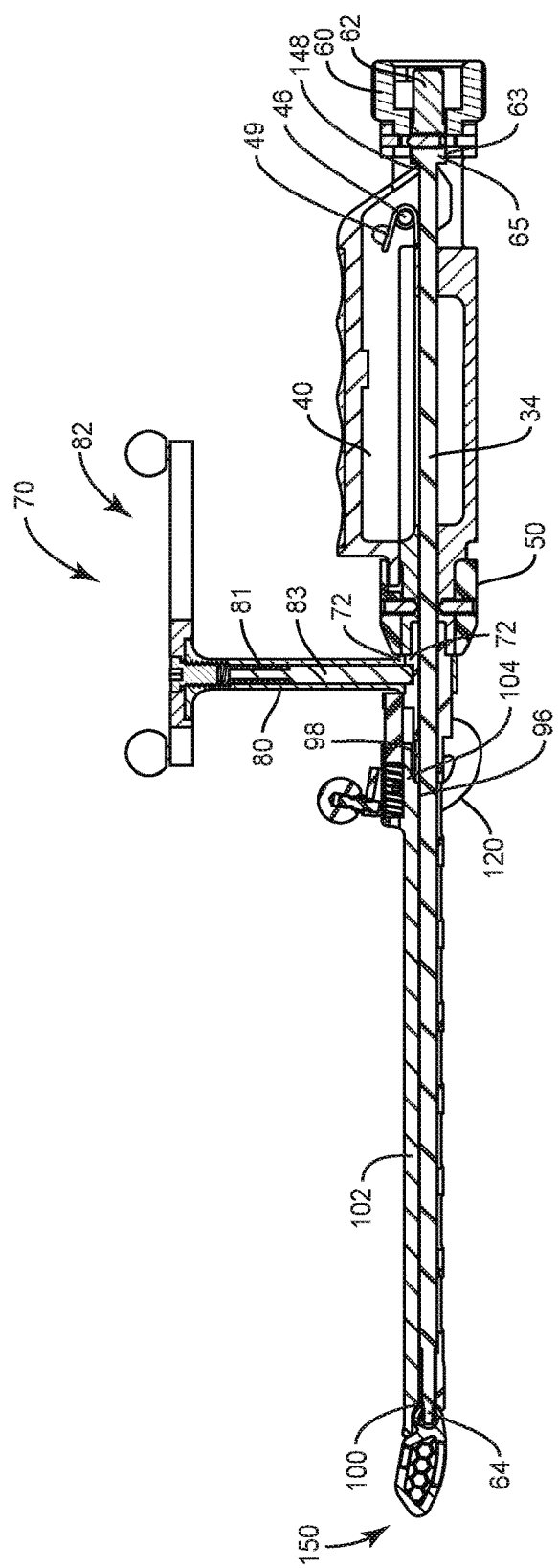
FIG. 4 is a cross-section view of the components shown in FIG. 1.

In some embodiments, grip 40 includes a biasing member, such as, for example, a torsion spring 49 disposed about pin 46, as shown in FIG. 4. Spring 49 includes legs that are connected with grip 40 and body 14. As such, spring 49 applies a biasing force to grip 40 to urge grip 40 into the non-locking orientation, as described herein. Grip 40 is manipulable to overcome the biasing force of spring 49 to pivot and/or rotate grip 40 for disposal in the locking orientation, as described herein. In some embodiments, grip 40 may be manually manipulable without a biasing member.

In some embodiments, the biasing member as described herein comprises a spring, a conical spring washer, a disc spring, a Belleville spring, a cupped spring washer, a coil spring, an elastomeric member, a clip, a leaf spring, gravity induced configuration, pneumatic configuration, hydraulic configuration and/or manual lever. In some embodiments, the biasing member may have a semi-rigid, rigid or elastic configuration, and/or have elastic properties, such as the elastic properties corresponding to the material examples described above, such that the biasing member provides a selective amount of movement between selected positions and orientations. In some embodiments, the biasing member may include a plurality of separately attachable or connectable portions or sections, such as bands or loops, or may be monolithically formed as a single continuous element. In some embodiments, the biasing member includes an axial element, such as, for example, a flexible shaft. In some embodiments, the biasing member has a solid disc or sphere shape.

Handle 22 includes a lock, such as, for example, a collar 50 configured to engage grip 40 for disposal in a locking orientation and a non-locking orientation relative to handle 22. Collar 50 includes a cavity, such as, for example, a cutout 52. Cutout 52 is configured to facilitate movement of grip 40 to a non-locking orientation, as described herein. Collar 50 is rotatable, in a clockwise direction and a counter-clockwise direction, between a locked orientation, as shown in FIG. 1, such that flange 48 is disposed within collar 50 and collar 50 resists and/or prevents pivoting of grip 40 relative to handle 22, and a non-locked orientation, as shown in FIG. 3, such that flange 48 is aligned with cutout 52 for movement therethrough and relative to handle 22. Alignment of cutout 52 with flange 48 allows grip 40 to disengage from collar 50 by passing through cutout 52. Disengagement of grip 40 from collar 50 allows for pivoting of grip 40 relative to handle 22. Grip 40 is configured to resist and/or prevent rotation of spinal implant 150 during a surgical procedure, as described herein.

Knob 60 is connected with handle 22 at end 26. Knob 60 is rotatable, in a clockwise direction and a counter-clockwise direction, to facilitate movement and/or translation of shaft 34 for moving and/or rotating spinal implant 150 to a selected orientation, as described herein. Shaft 34 extends between an end 62 and an end 64.

End 62 is engageable with knob 60 such that rotation of knob 60 causes shaft 34 to engage spinal implant 150 for movement and/or rotation relative to end 18. In some embodiments, shaft 34 is connected with knob 60 by a pin. In some embodiments, shaft 34 is connected with knob 60 by a threaded engagement. Shaft 34 includes a surface 63 that defines a circumferential flange 65. Flange 65 is configured for engagement with a flange 148 in the locking orientation of grip 40 to resist and/or prevent translation of shaft 34 relative to handle 22. When engaged in a locking orientation of grip 40, flange 148 applies a force to flange 65 in a mating engagement to apply a force and/or pressure to shaft 34. This force fixes position of shaft 34 relative to handle 22 and/or forms a pressure fit between end 18 and spinal implant 150. This configuration resists and/or prevents movement and/or rotation of spinal implant 150 relative to end 18. Flange 148 disengages from flange 65 for disposal of shaft 34 in a non-locked orientation. Disengagement of flange 148 from flange 65 releases the mating engagement and/or pressure fit between end 18 and spinal implant 150 to allow movement and/or rotation of spinal implant 150 relative to end 18. In some embodiments, grip 40 is selectively disposed in the locking and non-locking orientation to selectively fix and manipulate, move, translate, rotate and/or adjust position of spinal implant 150 relative to end 18 such that locking of grip 40 can be applied, released and/or re-applied for one or a plurality of iterations for positioning of spinal implant 150 with tissue. In some embodiments, grip 40 is selectively disposed in the locking and non-locking orientation to selectively fix and adjust position of spinal implant 150 in an angular range of 0 through 360 degrees relative to and about end 18. In some embodiments, grip 40 is selectively disposed in the locking and non-locking orientation to selectively fix and manipulate, move, translate, rotate and/or adjust position of spinal implant 150 relative to end 18 in a range of movement of spinal implant 150 between an insertion or delivery orientation, for example, as shown and described herein with regard to FIG. 1 and an implant orientation, as shown and described herein with regard to FIG. 3.

End 64 includes a surface 66 configured for mating engagement with a movable pin 156 disposed with spinal implant 150, as described herein. In some embodiments, end 64 is configured for threaded engagement with pin 156 upon actuation of knob 60. Actuation of knob 60 causes shaft 34 to draw spinal implant 150 into engagement with end 18 to fix spinal implant 150 with end 18 for delivery to a surgical site, as described herein. In some embodiments, surface 66 may have alternate surface configurations for mating engagement with a surface of spinal implant 150, such as, for example, grooved, rough, dimpled, polished, textured and/or a drive or socket, which may include a square, triangular, hexagonal, polygonal, star, torx or hexalobe cross section.

Figure 5:
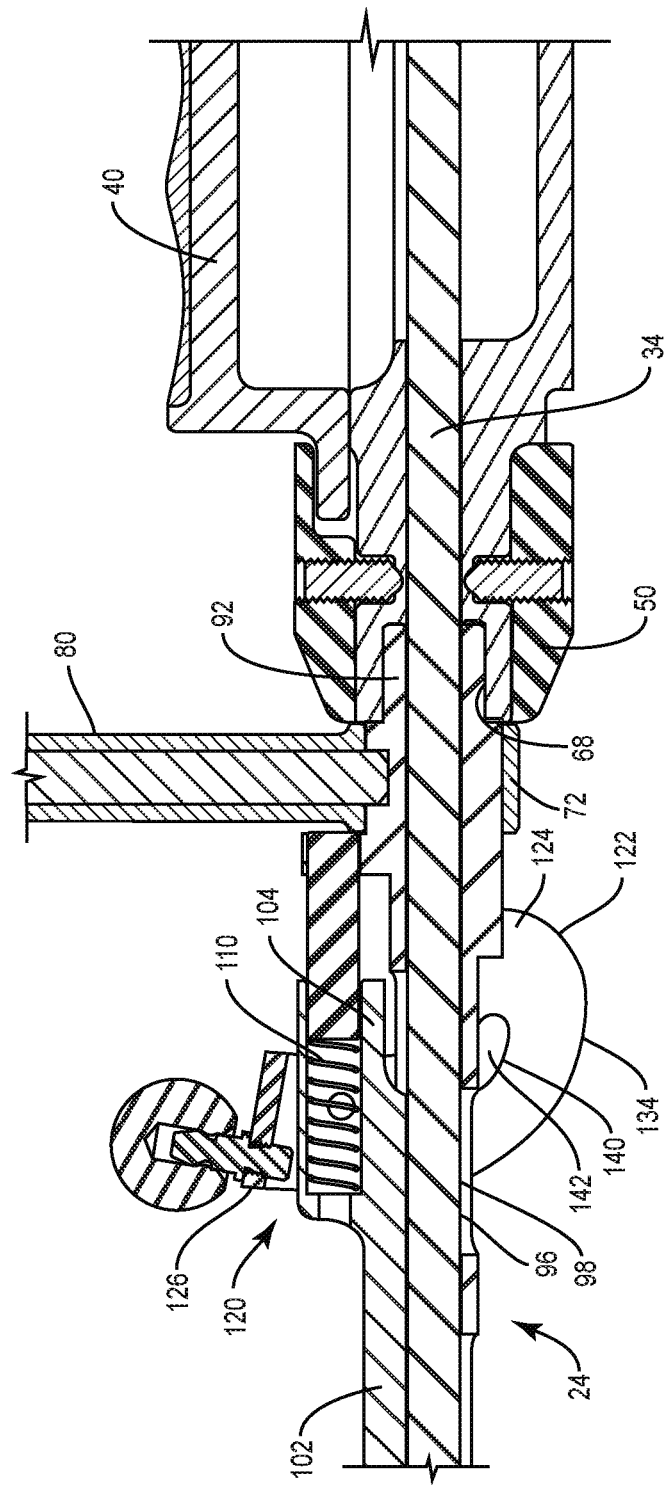
FIG. 5 is an enlarged break away view of the components shown in FIG. 4.
Figure 6:
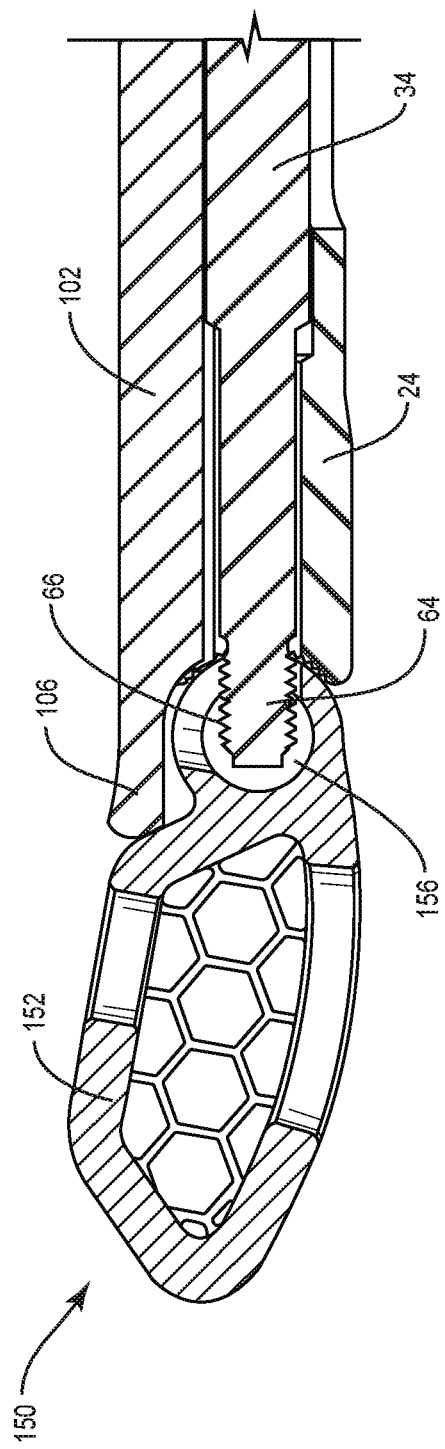
FIG. 6 is an enlarged break away view of the components shown in FIG. 4.

In some embodiments, handle 22 includes a mating cavity 68 disposed at end 28, as shown in FIG. 5. In some embodiments, mating cavity 68 may include a square, triangular, hexagonal, polygonal, star, torx or hexalobe cross section configured engage a correspondingly shaped portion of a surface that defines a mating surface 92 disposed with shaft 24, as described herein.

Body 14 is configured for connection with an image guide, which includes a navigation component 70, as described herein. Navigation component 70 is configured to generate a signal representative of a position of inserter 12. In some embodiments, an image guide as described herein may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 70 includes a collar 72 configured for disposal with a portion of body 14. In some embodiments, collar 72 is fixed with body 14. In some embodiments, collar 72 is rotatable relative to body 14 about axis A1. In some embodiments, collar 72 is connected with body 14 via a friction fit, pressure fit, interlocking engagement, mating engagement, dovetail connection, hook and loop closure, clips, barbs, tongue in groove, threaded, magnetic, key/keyslot, drill chuck and/or adhesive.

Collar 72 includes a post 80 extending therefrom. Post 80 defines an axis X1. Post 80 extends perpendicular to axis A1 and is rotatable with collar 72 about axis A1. In some embodiments, axis X1 may be disposed at alternate orientations relative to axis A1, such as, for example, parallel, transverse and/or other angular orientations, such as, acute or obtuse.

Navigation component 70 includes a tracking device having an emitter array 82 that is connected to collar 72 via post 80. In some embodiments, post 80 includes a cavity 81. In some embodiments, cavity 81 is configured to receive a threaded screw 83 configured to connect emitter array 82 with collar 72. Emitter array 82 is rotatable with collar 72 about axis A1. In some embodiments, emitter array 82 may be disposed at alternate orientations relative to axis A1, such as, for example, parallel, perpendicular, transverse and/or other angular orientations, such as, acute or obtuse.

Figure 7:
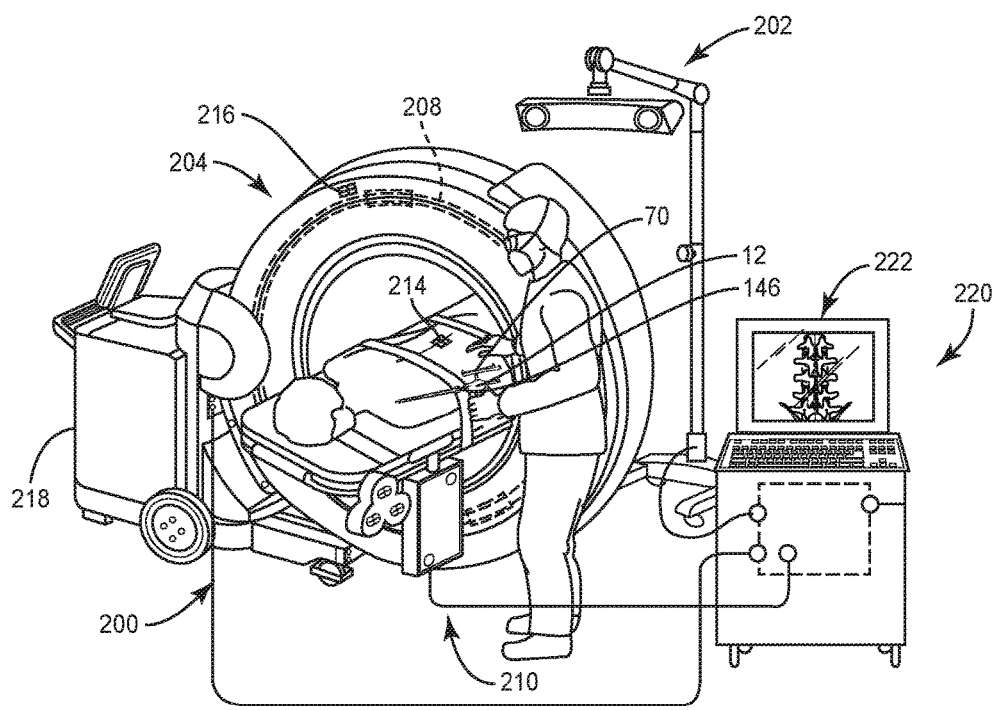
FIG. 7 is a perspective view of components of one embodiment of a surgical system in accordance with the principles of the present disclosure.

Emitter array 82 is configured for generating a signal to a sensor array 202, as shown in FIG. 7 and described herein, representing a three-dimensional spatial position and/or a trajectory of inserter 12 and/or spinal implant 150 relative to a portion of a patient's anatomy and/or a depth of inserter 12 and/or spinal implant 150 within the patient's anatomy for display on a monitor. Emitter array 82 includes four spaced apart arms having a substantially X-shape. Emitter array 82 includes markers, such as, for example, fiducials 84. Fiducials 84 appear in the image produced by a surgical navigation system 200 of surgical system 10 for use as a point of reference or a measure. Emitter array 82 generates signals representing the position of various body reference points of the patient's anatomy. In some embodiments, fiducials 84 include at least one light emitting diode. In some embodiments, fiducials 84 may include other tracking devices capable of being tracked by sensor array 202, such as, for example, a tracking device that actively generates acoustic signals, magnetic signals, electromagnetic signals and/or radiologic signals. In some embodiments, fiducials 84 may be removably attached to emitter array 82. In some embodiments, one or more of fiducials 84 each include a single ball-shaped marker.

Shaft 24 extends distally from handle 22 and includes end 18. Shaft 24 includes an end 90. End 90 includes cavity 92 configured for a mating engagement with mating surface 68. In some embodiments, cavity 92 may have various cross-section configurations, such as, for example, oval, oblong, triangular, rectangular, square, polygonal, irregular, uniform, non-uniform, variable, tubular and/or tapered.

Shaft 24 includes a surface 94 that defines a cavity, such as, for example, an axial channel 96. Channel 96 extends between an end 98 and an end 100. Channel 96 is configured for disposal of a longitudinal element, such as, for example, a rod 102. Rod 102 extends within channel 96 and includes an end 104 and an end 106 disposed adjacent end 18 and spinal implant 150 when attached with inserter 12.

Rod 102 is configured for translation relative to shaft 24 as spinal implant 150 is moved and/or rotated for positioning with tissue to provide indicia and/or display of an amount of manipulation, movement, translation and/or rotation of spinal implant 150 with tissue, such as, for example, an intervertebral space, as described herein. In some embodiments, rod 102 may have alternate cross section configurations, such as, for example, oval, oblong, triangular, square, hexagonal, polygonal, irregular, uniform, non-uniform and/or tapered.

In some embodiments, rod 102 includes a biasing member, such as, for example, a coil spring 110 mounted within a cavity of rod 102 and engageable with body 14. Spring 110 applies a biasing force to rod 102 to urge rod 102 into the insertion or delivery orientation, as described herein. With end 18 connected with spinal implant 150 in the insertion or delivery orientation, and handle 22 and shaft 34 disposed in the locking orientation, as described herein, spinal implant 150 is fixed with inserter 12. End 18 is fixed with spinal implant 150 and end 106 engages a surface of spinal implant 150 to provide indicia and/or a display of end 18 and/or spinal implant 150, as described herein.

End 104 includes an image guide 120. Image guide 120 includes an angle gauge 122 and a navigation component 180, as described herein. Gauge 122 measures a change in angle between an orientation, for example, a delivery orientation, as shown in FIG. 8, and an orientation, for example, an implant orientation, as shown in FIG. 9, as described herein. Image guide 120 represents and displays an angular measurement of the change in angle between selected relative orientations of spinal implant 150.

Gauge 122 extends between an end 124 and an end 126, as shown in FIG. 5. Gauge 122 rotates relative to shaft 24, as described herein. End 124 includes a ring 128, which is disposed about a pivot or pin 130 and configured to facilitate rotation of gauge 122 relative to shaft 24. In some embodiments, pin 130 is fixed with rod 102. In some embodiments, ring 128 is disposed with pin 130 in a substantially frictionless engagement to facilitate rotation of gauge 122 relative to shaft 24. In some embodiments, pin 130 is fixed with gauge 122 and rotatable relative to shaft 24 such that gauge 122 rotates relative to shaft 24. Gauge 122 pivots about pin 130 via ring 128 in response to translation of rod 102 such that gauge 122 rotates about pin 130, as described herein.

Gauge 122 includes arcuate sections 132, 134. Sections 132, 134 are disposed in a spaced apart relation. Section 132 includes a surface 136 that define a track 138. Section 134 includes a surface 140 that defines a track 142. Tracks 138, 142 are configured for moveable disposal of a member, such as, for example, a marker 144 disposed with rod 102, as shown in FIGS. 2 and 3.

In some embodiments, marker 144 is displaced and/or translated axially with rod 102 from an initial orientation, for example the delivery orientation of spinal implant 150, which indicates a resting, zero angle or calibration orientation of marker 144 and/or gauge 122. From the initial orientation, rod 102 engages spinal implant 150 to manipulate, move, translate and/or rotate spinal implant 150 such that marker 144 is displaced and/or translated axially with rod 102. In some embodiments, gauge 122 and/or marker 144 rotate about pin 130 relative to shaft 24 to measure a change in an angular orientation of gauge 122 and spinal implant 150 relative to inserter 12 and/or tissue, as described herein. In some embodiments, rod 102 translates in a proximal direction to overcome the biasing force of spring 110. In some embodiments, rod 102 may translate in a proximal direction and a distal direction in the implant orientation for positioning spinal implant 150 with tissue. In some embodiments, such translation causes gauge 122 to rotate from rest and/or equilibrium and a restoring force due to gravity is subjected to gauge 122.

Marker 144 causes gauge 112 to pivot or rotate about pin 130 such that marker 144 moves along tracks 138, 142 to indicate a measured angle of an implant orientation of spinal implant 150 relative to the initial orientation. In some embodiments, gauge 122 is rotated relative to marker 144 such that marker 144 is aligned with indicia 146 to represent and display an angular measurement of the angular difference of spinal implant 150 during insertion. In some embodiments, section 132 and/or section 134 include indicia 146 having information representing and displaying an angular measurement, as described herein. Pin 130 connects gauge 122 and marker 144 to shaft 24.

In some embodiments, indicia 146 includes graduated markings disposed along a surface of section 132 and/or section 134. In some embodiments, the markings display, represent and/or provide information relating to an angular range for measuring, selecting, adjusting and/or displaying an angle measured by gauge 122, as described herein. In some embodiments, the markings may include bi-laterally disposed grooves equidistantly spaced apart and corresponding to measured angular increments of indicia 146.

In some embodiments, indicia 146 includes markings that may be disposed in increments of 10 angular degrees. In some embodiments, indicia 146 may include an analog, such as, for example, a dial with a numerical indicator of angle and/or digital display, such as, for example, LED and/or LCD. In some embodiments, indicia 146 include human readable visual indicia, such as, for example, a label, color coding, alphanumeric characters or an icon. In some embodiments, indicia 146 include human readable tactile indicia, such as, for example, raised portions, lowered portions or Braille. In some embodiments, indicia 146 is a printed or written item in combination with a slot or groove, whereby the printed or written item is placed in the slot or groove to display information. In some embodiments, indicia 146 may be applied as an adhesive.

In some embodiments, gauge 122 and/or marker 144 and/or indicia 146 include radiolucent materials such as polymers. Radiomarkers may be included for identification under x-ray, fluoroscopy, CT or other imaging techniques. In some embodiments, navigation component 180 is configured to generate a signal representative of an angular position of end 106, end 18 and/or spinal implant 150. In some embodiments, navigation component 180 is configured to generate the signal as spinal implant 150 rotates. Navigation component 180 includes a fiducial 182. Fiducial 182 appears in an image produced by surgical navigation system 200 for use as a point of reference or a measure. Fiducial 182 generates signals representing positioning of gauge 122 and an angular position of spinal implant 150. In some embodiments, fiducial 182 generates signals representing a position of spinal implant 150 being rotated to a selected orientation with tissue. In some embodiments, fiducial 182 generates signals representing a selected plane of a body, such as, for example, a transverse plane. In some embodiments, fiducial 182 includes at least one light emitting diode. In some embodiments, fiducial 182 may include other tracking devices capable of being tracked by sensor array 202, such as, for example, a tracking device that actively generates acoustic signals, magnetic signals, electromagnetic signals, radiologic signals. In some embodiments, fiducial 182 may be removably attached to rod 102. In some embodiments, fiducial 182 may include a single ball-shaped marker. In some embodiments, fiducial 182 may include one or a plurality of markers.

Navigation component 180 is disposed with gauge 122 and is rotatable to provide indicia and/or display the angular orientation and/or a trajectory of spinal implant 150 relative to inserter 12, a portion of a patient's anatomy and/or a depth of end 18 and/or spinal implant 150 within the patient's anatomy. Rod 102 is oriented with shaft 24 and engageable with a surface of spinal implant 150 between a proximal position and a distal position relative to body 14 such that fiducial 182 provides the angular indicia and/or display of spinal implant 150.

End 106 is configured for disposal adjacent a surface of spinal implant 150 such that rotation of spinal implant 150 causes rod 102 to translate within channel 96, as shown in FIGS. 8 and 9. Translation of rod 102 causes fiducial 182 to rotate to indicate position, movement and/or rotation of spinal implant 150.

In some embodiments, the proximal position of rod 102 corresponds to spinal implant 150 being connected with end 18 and disposed in an insertion or delivery orientation, as shown in FIG. 8. In some embodiments, in the insertion or delivery orientation, spinal implant 150 is disposed in axial alignment with shaft 24. In some embodiments, the distal position of rod 102 corresponds to spinal implant 150 being connected with end 18 and disposed in an implant orientation, as shown in FIG. 9. In some embodiments, the two-dimensional spatial position and/or trajectory includes a plane of the patient's anatomy, such as, for example, a transverse plane.

Spinal implant 150 includes a vertebral engaging surface 152 and a vertebral engaging surface 154. In some embodiments, the cross-sectional geometry of spinal implant 150 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surfaces 152, 154 may be smooth, even, rough, textured, porous, semi-porous, dimpled and/or polished.

In some embodiments, spinal implant 150 includes a cavity configured for disposal of a pin 156 to facilitate rotating and/or pivoting of spinal implant 150 relative to end 18. Pin 156 includes a surface configured for engagement with end 64 of shaft 34. In some embodiments, pin 156 includes a threaded inner surface that mates with threads 66 to facilitate connection of spinal implant 150 with inserter 12 for positioning of spinal implant 150 with tissue.

In some embodiments, spinal implant 150 is rotatable relative to pin 156 through a selected angular range. In some embodiments, spinal implant 150 is selectively rotatable relative to pin 156. In some embodiments, spinal implant 150 is passively rotatable relative to pin 156 such that manipulation of inserter 12 connected with spinal implant 150 during insertion of spinal implant 150 with a vertebral space causes spinal implant 150 to rotate relative to pin 156 due to engagement with end 18 and resistance of tissue.

Inserter 12 is configured for disposal adjacent a surgical site such that navigation component 70 and/or navigation component 180 are oriented relative to sensor array 202 to facilitate communication between navigation component 70 and/or navigation component 180, and sensor array 202 during a surgical procedure, as described herein. In some embodiments, sensor array 202 receives signals from navigation component 70 to provide a three-dimensional spatial position and/or a trajectory of inserter 12 and/or spinal implant 150 relative to a portion of a patient's anatomy and/or a depth of inserter 12 and/or spinal implant 150 within the patient's anatomy for display on a monitor. In some embodiments, sensor array 202 receives signals from navigation component 180 disposed with gauge 122 to provide an angular position of end 106, end 18 and/or spinal implant 150. See, for example, similar surgical navigation components and their use as described in U.S. Pat. Nos. 6,021,343, 6,725,080, 6,796,988, the entire contents of each of these references being incorporated by reference herein.

Surgical navigation system 200 is configured for acquiring and displaying medical imaging, such as, for example, x-ray images appropriate for a given surgical procedure, as shown in FIG. 7. In some embodiments, pre-acquired images of a patient are collected. In some embodiments, surgical navigation system 200 can include an O-arm® imaging device 204 sold by Medtronic Navigation, Inc. having a place of business in Louisville, Colo., USA. Imaging device 204 may have a generally annular gantry housing that encloses an image capturing portion 208.

In some embodiments, image capturing portion 208 may include an x-ray source or emission portion and an x-ray receiving or image receiving portion located generally or as practically possible 180 degrees from each other and mounted on a rotor (not shown) relative to a track of image capturing portion 208. Image capturing portion 208 can be operable to rotate 360 degrees during image acquisition. Image capturing portion 208 may rotate around a central point or axis, allowing image data of the patient to be acquired from multiple directions or in multiple planes. Surgical navigation system 200 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 200 can include C-arm fluoroscopic imaging systems, which can generate three-dimensional views of a patient. The position of image capturing portion 208 can be precisely known relative to any other portion of imaging device 204. In some embodiments, a precise knowledge of the position of image capturing portion 208 can be used in conjunction with a tracking system 210 to determine the position of image capturing portion 208 and the image data relative to the patient.

Tracking system 210 can include various portions that are associated or included with surgical navigation system 200. In some embodiments, tracking system 210 can also include a plurality of types of tracking systems, such as, for example, an optical tracking system that includes an optical localizer, such as, for example, sensor array 202 and/or an EM tracking system that can include an EM localizer. Various tracking devices can be tracked with tracking system 210 and the information can be used by surgical navigation system 200 to allow for a display of a position of an item, such as, for example, a patient tracking device 214, an imaging device tracking device 216, and an instrument tracking device, such as, for example, navigation components 70, 180, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to computer 218 where they may be forwarded to surgical navigation computer 220. Image transfer may be performed over a standard video connection or a digital link including wired and wireless. Computer 220 provides the ability to display, via monitor 222, as well as save, digitally manipulate, or print a hard copy of the received images. In some embodiments, images may also be displayed to the surgeon through a heads-up display.

In some embodiments, surgical navigation system 200 provides for real-time tracking of inserter 12 and spinal implant 150. Sensor array 202 is located in such a manner to provide a clear line of sight with navigation components 70, 180, as described herein. In some embodiments, navigation components 70, 180 communicate with sensor array 202 via infrared technology. Sensor array 202 is coupled to computer 220, which may be programmed with software modules that analyze signals transmitted by sensor array 202 to determine the position of each object in a detector space. A processor sends the information to monitor 222, which provides a visual representation of the position of inserter 12 and spinal implant 150 relative to the patient's anatomy to allow the medical practitioner to move inserter 12 and spinal implant 150 to a desired location within the patient's anatomy.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae V, as shown in FIGS. 8 and 9. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body, such as, for example, vertebrae V. In some embodiments, the components of surgical system 10 may be employed with one or a plurality of vertebra, such as, for example, vertebra V1 and vertebra V2. To treat a selected section of vertebrae V, a medical practitioner obtains access to a surgical site including vertebrae V in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including inserter 12, as described herein, adjacent an area within the patient's body, such as, for example, vertebra V1 and vertebra V2. In some embodiments, a preparation instrument (not shown) is employed to remove disc tissue, fluids, adjacent tissues and/or bone, and scrape and/or remove tissue from endplate surfaces of vertebra V1 and/or endplate surface of vertebra V2. In some embodiments, the size of spinal implant 150 is selected after trialing. In some embodiments, spinal implant 150 is visualized by fluoroscopy and oriented before introduction into the vertebral space.

Inserter 12 is connected with spinal implant 150, as described herein, for disposal in an insertion or delivery orientation, as described herein. Grip 40 is initially disposed in the non-locking orientation and manipulated for rotation about pin 46 to the locking orientation, as shown in FIG. 8 and described herein. Collar 50 is disposed in the locked orientation, as described herein. Knob 60 is rotated causing shaft 34 to engage pin 156 to connect spinal implant 150 with inserter 12, as described herein, and draw ends 18, 106 into engagement with spinal implant 150.

Spinal implant 150 is disposed in a selected and fixed position relative to end 18 such that spinal implant 150 is axially aligned with shaft 24. Inserter 12 is manipulated to deliver spinal implant 150 to the vertebral space between vertebrae V1, V2. Sensor array 202 receives signals from navigation component 70 to provide a three-dimensional spatial position and/or a trajectory of inserter 12 and/or spinal implant 150 relative to the vertebral space between vertebrae V1, V2 and/or a depth of inserter 12 and/or spinal implant 150 within the vertebral space for display on monitor 222.

Inserter 12 selectively disposes spinal implant 150 with the vertebral space between vertebrae V1, V2, as shown in FIG. 8. With end 18 connected with spinal implant 150 in the insertion or delivery orientation, end 106 engages a surface of spinal implant 150 to provide the indicia and/or display of end 18 and/or spinal implant 150 in connection with fiducial 182, as described herein. Collar 50 is rotated to the non-locked orientation, as described herein. Grip 40 is released for rotation about pin 46 to the non-locking orientation, as shown in FIG. 9 and described herein. The pressure fit between ends 18, 106 is released and spinal implant 150 is movable and/or rotatable relative to end 18, 106.

Manipulation of inserter 12 causes spinal implant 150 to move and/or rotate about pin 156, as described herein, into position with the vertebral space between vertebrae V1, V2. As spinal implant 150 is manipulated, moved, translated and/or rotated in the implant orientation for positioning spinal implant 150 with the vertebral space between vertebrae V1, V2, spinal implant 150 is engaged with rod 102 such that rod 102 translates in a proximal direction. Such translation causes gauge 122 to rotate about pin 130 to align marker 144 with indicia 146 to indicate a measured angle of the implant orientation for positioning spinal implant 150 with the vertebral space between vertebrae V1, V2 relative to the insertion or delivery orientation, as described herein.

In some embodiments, indicia 146 is visibly read by a practitioner viewing gauge 122. In some embodiments, sensor array 202 receives signals from navigation component 180 to provide an angular position of end 106, end 18 and/or spinal implant 150, for example, within a transverse plane of vertebra V. In some embodiments, locking and unlocking of grip 40 allows for selective movement and/or rotation of spinal implant 150 in the implant orientation.

Inserter 12 is disengaged from spinal implant 150. In some embodiments, spinal implant 150 provides height restoration between vertebral bodies, decompression, restoration of sagittal and/or coronal balance and/or resistance of subsidence into vertebral endplates. In some embodiments, surgical system 10 includes a plurality of spinal implants 150. In some embodiments, employing a plurality of spinal implants 150 can optimize the amount of vertebral space that can be spaced apart such that the joint spacing dimension can be preselected. The plurality of spinal implants 150 can be oriented in a side by side engagement, spaced apart and/or staggered.

In some embodiments, surgical system 10 may comprise various instruments including the configuration of the present disclosure, such as, for example, inserters, extenders, reducers, spreaders, distracters, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, such as, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of surgical system 10 are removed from the surgical site and the incision is closed.

In one embodiment, as shown in FIGS. 10-13, surgical system 10, similar to the systems and methods described above with regard to FIGS. 1-9, includes an inserter 312. Inserter 312 includes a body 314 that defines a longitudinal axis A2, similar to body 14 described herein. Body 314 extends between an end 316 and an end 318. Body 314 includes an outer sleeve 320. Outer sleeve 320 includes a handle 322, similar to handle 22 described herein. Outer surface 320 includes a shaft 324, similar to shaft 24 described herein. In some embodiments, handle 322 may be assembled with shaft 324, as described herein.

Handle 322 includes a cavity 332 configured for disposal of a shaft 334, similar to shaft 34 described herein. Shaft 334 is configured to connect spinal implant 150, described herein, with inserter 312. Handle 322 is configured to facilitate manipulating, moving, translating and/or rotating spinal implant 150, as described herein. Handle 322 includes an actuator that includes a pivoting grip 340, similar to grip 40 described herein. The actuator includes a knob 360, similar to knob 60 described herein. Grip 340 includes a flange 348 configured to facilitate locking and unlocking of grip 340 relative to handle 322, similar to flange 48 described herein.

Figure 11:
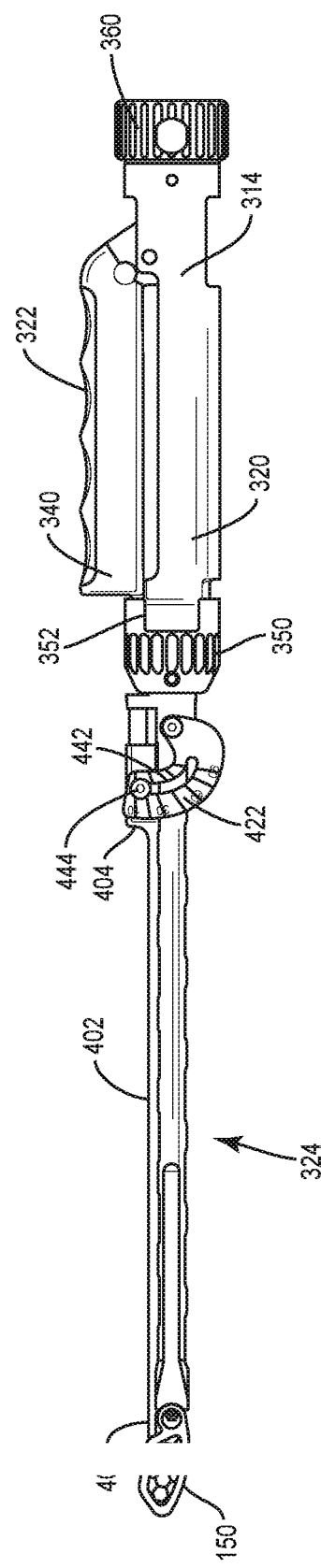
FIG. 11 is a side view of the components shown in FIG. 10.
Figure 13:
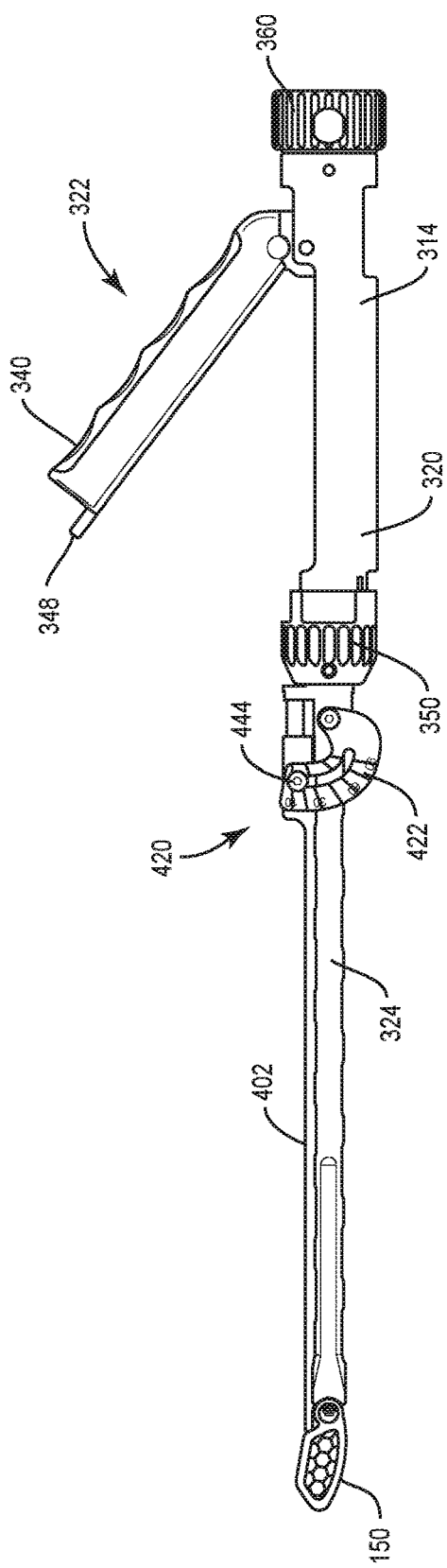
FIG. 13 is a side view of the components shown in FIG. 10.

Grip 340 is configured to rotate and/or pivot relative to axis A2 between a locking orientation, as shown in FIG. 11, and a non-locking orientation, as shown in FIG. 13, of grip 340 with shaft 334. Locking of grip 340 resists and/or prevents translation of shaft 334, for example, such that spinal implant 150 is disposed in a selected and fixed position relative to end 318, similar to that described herein. Rotating grip 340 into a non-locking orientation allows for movement and/or translation of shaft 334 relative to body 314 to facilitate movement and/or rotation of spinal implant 150 relative to end 318, as described herein. Handle 322 includes a collar 350, similar to collar 50 described herein. Collar 350 includes a cutout 352, similar to cutout 52 described herein. Cutout 352 is configured to facilitate movement of grip 340 to a non-locking orientation, as described herein. Collar 350 is configured to engage grip 340 for disposal in a locking orientation and a non-locking orientation relative to handle 322. In some embodiments, grip 340, similar to grip 40 described herein, is selectively disposed in the locking and non-locking orientation to selectively fix and manipulate, move, translate, rotate and/or adjust position of spinal implant 150 relative to end 318.

Knob 360 is rotatable, in a clockwise direction and a counter-clockwise direction, to facilitate movement and/or translation of shaft 334 for moving and/or rotating spinal implant 150 to a selected orientation, as described herein. Actuation of knob 360 causes shaft 334 to draw spinal implant 150 into engagement with end 318 to fix spinal implant 150 with end 318 for delivery to a surgical site, as described herein.

Shaft 324 extends distally from handle 322 and includes end 318. Shaft 324 includes an axial channel 396. Channel 396 is configured for disposal of a rod 402, similar to rod 102 described herein. Rod 402 extends within channel 396 and includes an end 404 and an end 406 disposed adjacent end 318 and spinal implant 150 when attached with inserter 312. Rod 402 translates relative to shaft 324 and spinal implant 150 moves and/or rotates for positioning with tissue, such as, for example, an intervertebral space, as described herein. Rod 402 is oriented with shaft 324 and engageable with a surface of spinal implant 150 between a proximal position and a distal position relative to body 314.

In some embodiments, rod 402 includes a biasing member, similar to coil spring 114, as described herein, that applies a biasing force to rod 402 to urge rod 402 into the insertion or delivery orientation, as described herein. End 404 includes an image guide 420 having an angle gauge 422, similar to gauge 122 described herein. Gauge 422 represents and displays an angular measurement of the change in angle between selected relative orientations of spinal implant 150. Gauge 422 rotates relative to shaft 24, as described herein. Gauge 422 includes tracks 438, 442 configured for moveable disposal of a marker 444, as described herein. Gauge 422 measures a change in angular orientation of spinal implant 150 between an orientation, for example, a delivery orientation and an orientation, for example, an implant orientation, as described herein.

With end 318 connected with spinal implant 150 in the insertion or delivery orientation, and handle 322 and shaft 334 disposed in the locking orientation, as described herein, spinal implant 150 is fixed with inserter 312. End 318 is fixed with spinal implant 150 and end 406 engages a surface of spinal implant 150. As spinal implant 150 is manipulated, moved, translated and/or rotated in the implant orientation for positioning spinal implant 150 with tissue, spinal implant 150 is engaged with rod 402 such that rod 402 translates in a proximal direction to overcome the biasing force of the biasing member. In some embodiments, rod 402 may translate in a proximal direction and a distal direction in the implant orientation for positioning spinal implant 150 with tissue. In some embodiments, rod 402 may be manually manipulable without a biasing member.

Figure 12:
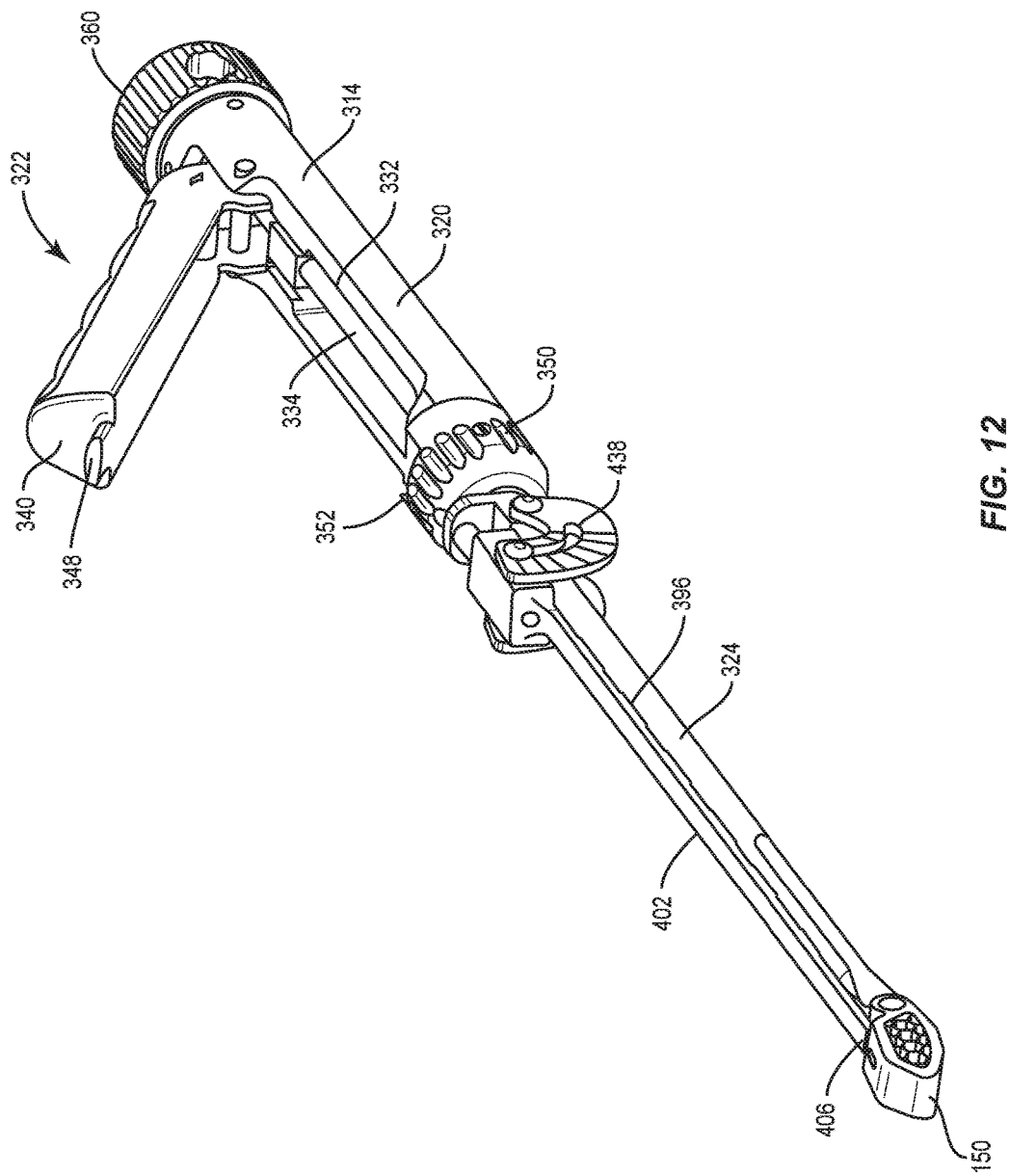
FIG. 12 is a perspective view of the components shown in FIG. 10.

In use, similar to the methods and surgical procedures employing surgical system 10 and inserter 12, inserter 312 selectively disposes spinal implant 150 with the vertebral space between vertebrae V1, V2, as shown in FIG. 12. With end 318 connected with spinal implant 150 in the insertion or delivery orientation, end 406 engages a surface of spinal implant 150. Collar 350 is rotated to the non-locked orientation, as described herein. Grip 340 is released for rotation to the non-locking orientation, as shown in FIG. 13 and described herein. A pressure fit between ends 318, 406 is released and spinal implant 150 is movable and/or rotatable relative to end 318, 406.

Manipulation of inserter 312 causes spinal implant 150 to move and/or rotate, as described herein, into position with the vertebral space between vertebrae V1, V2. As spinal implant 150 is manipulated, moved, translated and/or rotated in the implant orientation for positioning spinal implant 150 with the vertebral space between vertebrae V1, V2, spinal implant 150 is engaged with rod 402 such that rod 402 translates in a proximal direction. Gauge 422 provides visual indicia of a measured angle of the implant orientation for positioning spinal implant 150 with the vertebral space between vertebrae V1, V2 relative to the insertion or delivery orientation, similar to that described herein. In some embodiments, locking and unlocking of grip 340 allows for selective movement and/or rotation of spinal implant 150 in the implant orientation. Inserter 312 is disengaged from spinal implant 150.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    a member comprising a shaft and a longitudinal element disposed in a channel of the shaft, the shaft being connected with a spinal implant defining an implant axis, the longitudinal element being configured to translate relative to the shaft to move the implant between a first orientation in which the implant axis extends at a first angle relative to a member axis defined by the shaft and a second orientation in which the implant axis extends at a second angle relative to the member axis; and
    an image guide connected with the longitudinal element and being oriented to represent an implant angle measuring the first angle relative to the second angle.

2. A surgical instrument as recited in claim 1, further comprising a second image guide connected with the member and being oriented to communicate a signal representative of a position of the member.

3. A surgical instrument as recited in claim 1, wherein the image guide includes indicia representing the implant angle.

4. A surgical instrument as recited in claim 1, wherein the image guide includes a rotational gauge having indicia representing the implant angle.

5. A surgical instrument as recited in claim 1, wherein the image guide includes indicia representing the implant angle, the indicia including a marker and graduated markings disposed with the member.

6. A surgical instrument as recited in claim 1, wherein the first orientation includes a zero angle reference.

7. A surgical instrument as recited in claim 1, wherein the image guide is oriented relative to a sensor to communicate a signal representative of the implant angle.

8. A surgical instrument as recited in claim 1, wherein the member includes an actuator connected with the longitudinal element that translates an end of the member connected with the spinal implant.

9. A surgical instrument as recited in claim 8, wherein the actuator includes a pivotable grip handle.

10. A surgical instrument as recited in claim 8, wherein the member includes a lock engageable with the actuator to resist and/or prevent rotation of the spinal implant.

11. A surgical instrument as recited in claim 1, wherein the image guide comprises an emitter mounted with the longitudinal element.

12. A surgical instrument as recited in claim 1, wherein the image guide is oriented relative to a sensor to communicate a signal representative of the implant angle and the sensor communicates with a processor to generate data for display of an image from a monitor, the image representing position of the member relative to a body and the spinal implant relative to the member.

13. A surgical instrument as recited in claim 1, further comprising a second image guide oriented to communicate a signal representative of a position of the member, the second image guide comprising a collar that is rotatable relative to the shaft about the member axis.

14. A surgical instrument as recited in claim 1, wherein the member includes an inner shaft comprising a threaded outer surface that engages a threaded inner surface of the spinal implant.

15. A surgical instrument as recited in claim 14, wherein an outer surface of the inner shaft engages an outer surface of the longitudinal element.

16. A surgical instrument as recited in claim 14, wherein the member includes a handle having a knob that is rotatable relative to the shaft about the member axis, the knob being rotatable to rotate the inner shaft.

17. A surgical instrument as recited in claim 14, wherein the implant includes a body and a pin that is rotatable relative to the body, the pin including the threaded inner surface.

18. A surgical instrument as recited in claim 1, wherein the longitudinal element includes opposite first and second ends, the first end including the image guide, the second end directly engaging the implant.

19. A surgical instrument comprising:
a spinal implant defining an implant axis;
an outer body defining an axial channel; and
an inner shaft disposed within the axial channel and engaging the spinal implant, the inner shaft being translatable relative to the outer body to move the implant between a first orientation in which the implant axis extends at a first angle relative to a member axis defined by the outer body and a second orientation in which the implant axis extends at a second angle relative to the member axis, the inner shaft including an image guide oriented to represent an angle measuring the first angle relative to the second angle.

20. A surgical instrument comprising:
a member comprising a shaft defining an axis and a longitudinal element disposed in an axial channel of the shaft;
a spinal implant connected with the shaft and defining an implant axis, the longitudinal element being configured to translate relative to the shaft to move the implant between a first orientation in which the implant axis extends at a first angle relative to a member axis defined by the shaft and a second orientation in which the implant axis extends at a second angle relative to the member axis; and
an image guide that is fixed relative to the longitudinal element and oriented to represent an angle measuring the the first angle relative to the second angle,
wherein the member includes an actuator connected with the longitudinal element that translates an end of the member connected with the spinal implant.

* * * * *